(12) United States Patent
Mintz et al.

(10) Patent No.: US 6,506,884 B1
(45) Date of Patent: Jan. 14, 2003

(54) VARIANT OF VASCULAR ENDOTHELIAL GROWTH FACTOR

(75) Inventors: Liat Mintz, Ramat Hasharon (IL); Kinneret Savitzky, Tel Aviv (IL); Sharon Engel, Ramat Hasharon (IL)

(73) Assignee: Compugen Ltd., Tel Aviv (IL)

( * ) Notice: Subject to any disclaimer, the term of this patent is extended or adjusted under 35 U.S.C. 154(b) by 0 days.

(21) Appl. No.: 09/519,476

(22) Filed: Mar. 6, 2000

(30) Foreign Application Priority Data

Mar. 5, 1999 (IL) .................................................. 128852

(51) Int. Cl.[7] ........................... A61K 38/18; G01N 33/53
(52) U.S. Cl. ........................ 530/399; 530/350; 435/7.1; 435/69.1; 435/7.8; 435/252.3; 514/2; 514/8
(58) Field of Search ................................. 530/350, 399; 435/69.1, 69.4, 71.1, 71.2, 471, 325, 320.1, 252.3, 254.11; 514/2, 8, 12

(56) References Cited

U.S. PATENT DOCUMENTS

| 5,194,596 | A | * | 3/1993 | Tischer et al. ............... 530/399 |
| 5,935,820 | A | * | 8/1999 | Hu et al. .................... 435/69.4 |
| 6,022,541 | A | * | 2/2000 | Senger et al. ............. 424/172.1 |

OTHER PUBLICATIONS

Ferrara, N., "Vascular Endothelial Growth Factor," *European Journal of Cancer,* vol. 32A, No. 14, pp. 2413–2422, (1996).

* cited by examiner

*Primary Examiner*—Gary L. Kunz
*Assistant Examiner*—Sarada C Prasad
(74) *Attorney, Agent, or Firm*—Birch Stewart Kolasch & Birch LLP

(57) ABSTRACT

The invention concerns novel nucleic acid sequences and amino acid sequences of a novel variant of vascular endothelial growth factor (VEGF). The invention further concerns expression vectors and host cells containing said sequences as well as pharmaceutical compositions and detection methods using said sequences.

6 Claims, 3 Drawing Sheets

VARIANT OF VASCULAR ENDOTHELIAL GROWTH FACTOR

FIELD OF THE INVENTION

The present invention concerns novel nucleic acid sequences, vectors and host cells containing them, amino acid sequences encoded by said sequences, and antibodies reactive with said amino acid sequences, as well as pharmaceutical compositions comprising any of the above. The present invention further concerns methods for screening for candidate activator or deactivators utilizing said amino acid sequences.

BACKGROUND OF THE INVENTION

Vascular endothelial growth factor (VEGF) is a heparin-binding growth factor specific for vascular endothelial cells that is able to induce angiogenesis in vivo. DNA sequencing suggests the existence of several molecular species of VEGF. VEGFs are secreted proteins in contrast to other endothelial cell mitogens such as acidic or basic fibroblast growth factors and platelet-derived endothelial cell growth factors. VEGF was found to augment human growth by inducing neovascularization. Thus it was suggested that neutralization of VEGF activity may have clinical application in inhibiting malignant cells-induced angiogenesis, decreasing blood supply to the cancerous tissue, leading eventually to its destruction. VEGF has various other functions on endothelial cells, the most prominent of which is the induction of proliferation and differentiation. It was found to be capable of preventing serum starvation-induced apoptosis and this inhibition may represent a major aspect of the regulatory activity of VEGF on vascular endothelium.

VEGF was also found to be involved in the development and the growth of ovarian corpus luteum (CL), since its development is dependent on the growth of new capillary vessels. It has been reported that Flt-1 receptors which inhibit vascular endothelial growth factor bioactivity, resulted in complete separation of corpus luteum angiogenesis in a rat model of hormonally induced ovulation, indicated that VEGF is essential for CL angiogenesis and may be involved in the control of fertility and treatment of ovarian disorders characterized by hypervascularity and hyperplasia.

The human VEGF gene has been recently assigned to chromosome 6p21.2. cDNA sequence analysis of a variety of human VEGF clones had initially indicated that VEGF may exist as one of four different molecular species, having respectively, 121, 165, 189 and 206 amino acids (VEGF$_{121}$, VEGF$_{165}$, BEGF$_{206}$). Alternative exon splicing of a single VEGF gene is the basis for this molecular heterogeneity, VEGF$_{165}$ lacks the residues encoded by exon 6, while VEGF$_{121}$ lacks the residues encoded by exons 6 and 7. VEGF$_{189}$ has an insertion of 24 amino acids highly enriched in basic residues and VEGF$_{206}$ has an additional insertion of 17 amino acids. VEGF$_{165}$ is the predominant isoform secreted by a variety of normal and transformed cells. Transcripts encoding VEGF$_{121}$ and VEGF$_{189}$ are detected in the majority of cells and tissues expressing the VEGF gene. In contrast, VEGF$_{206}$ is a very rare form.

Native VEGF is a basic, heparin-binding, homodimeric glycoprotein of 45 kDA. These properties correspond to those of VEGF$_{165}$. VEGF$_{121}$ is an acidic polypeptide that fails to bind to heparin. VEGF$_{189}$ and VEGF$_{200}$ are more basic and bind to heparin with greater affinity than VEGF$_{165}$. VEGF$_{121}$ is a freely soluble protein; VEGF$_{165}$ is also secreted, although a significant fraction remains bound to the cell surface and the extracellular matrix (ECM). VEGF$_{189}$ and VEGF$_{206}$ are almost completely sequestered in the ECM, but may be released in a soluble form by heparin or heparinase. Also, these long forms may be released by plasmin following cleavage at the COOH terminus (Ferrara, N., *European J. of Cancer*, 32A(14):2413–2422 (1996)).

GLOSSARY

In the following description and claims use will be made, at times, with a variety of terms, and the meaning of such terms as they should be construed in accordance with the invention is as follows:

"Vascular endothelial growth factor variant (VEGFV) nucleic acid sequence"—the sequence shown in SEQ ID NO: 1, sequences having at least 70% identity to said sequence and fragments of the above sequences of least 20 b.p. long. This sequence is a sequence coding for a novel alternative splice variant of the native VEGF. While the known VEGF peptides include 206, 189, 105 or 121 amino acids, the novel VEGF variant peptide of the invention includes only 141 amino acids, −27 of which being in the signal peptide and 114 being present in the mature protein. According to the terminology used in the publication of Ferrara (supra) this new variant should be termed VEGF$_{114}$.

"Vascular endothelial growth factor variant (VEGFV product)—also referred at times as the "VEGFV protein" or "VEGFV polypeptide"—is an amino acid sequence having the first 141 amino acids of the native VEGF. This naturally occurring sequence is the result of alternative splicing. The amino acid sequence may be a peptide, a protein, as well as peptides or proteins having chemically modified amino acids (see below) such as a glycopeptide or glycoprotein. An example of an VEGFV product is shown in SEQ ID NO: 2. The term also includes analogues of said sequences in which one or more amino acids has been added, deleted, substituted (see below) or chemically modified (see below) as well as fragments of this sequence having at least 10 amino acids.

"Nucleic acid sequence"—a sequence composed of DNA nucleotides, RNA nucleotides or a combination of both types and may includes natural nucleotides, chemically modified nucleotides and synthetic nucleotides.

"Amino acid sequence"—a sequence composed of any one of the 20 naturally appearing amino acids, amino acids which have been chemically modified (see below), or composed of synthetic amino acids.

"Fragment of VEGFV product"—a polypeptide which has an amino acid sequence which is the same as part of but not all of the amino acid sequence of the VEGFV product.

"Fragments of VEGFV nucleic acid sequence" a continuous portion, preferably of about 20 nucleic acid sequences of the VEGFV nucleic acid sequence.

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. [Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Chemically modified"—when referring to the product of the invention, means a product (protein) where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

"Biologically active"—refers to the VEGFV product having structural, regulatory or biochemical functions of the naturally occurring VEGFV product, for example the same effect on vascular endothelial cells.

"Immunologically active" defines the capability of a natural, recombinant or synthetic VEGFV product, or any fragment thereof, to induce a specific immune response in appropriate animals or cells and to bind with specific antibodies. Thus, for example, a biologically active fragment of VEGFV product denotes a fragment which retains some or all of the immunological properties of the VEGFV product, e.g can bind specific anti-VEGFV product antibodies or which can elicit an immune response which will generate such antibodies or cause proliferation of specific immune cells which produce VEGFV.

"Optimal alignment"—is defined as an alignment giving the highest percent identity score. Such alignment can be performed using a variety of commercially available sequence analysis programs, such as the local alignment program LALIGN using a ktup of 1, default parameters and the default PAM. A preferred alignment is the one performed using the CLUSTAL-W program from MacVector (TM), operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

"Having at least X% identity"—with respect to two amino acid or nucleic acid sequence sequences, refers to the percentage of residues that are identical in the two sequences when the sequences are optimally aligned. Thus, 70% amino acid sequence identity means that 70% of the amino acids in two or more optimally aligned polypeptide sequences are identical.

"Isolated nucleic acid molecule having an VEGFV nucleic acid sequence"—is a nucleic acid molecule that includes the coding VEGFV nucleic acid sequence. Said isolated nucleic acid molecule may include the VEGFV nucleic acid sequence as an independent insert; may include the VEGFV nucleic acid sequence fused to an additional coding sequences, encoding together a fusion protein in which the VEGFV coding sequence is the dominant coding sequence (for example, the additional coding sequence may code for a signal peptide); the VEGFV nucleic acid sequence may be in combination with non-coding sequences, e.g., introns or control elements, such as promoter and terminator elements or 5' and/or 3' untranslated regions, effective for expression of the coding sequence in a suitable host; or may be a vector in which the VEGFV protein coding sequence is a heterologous.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

"Antibody"—refers to IgG, IgM, IgD, IgA, and IgG antibody. The definition includes polyclonal antibodies or monoclonal antibodies. This term refers to whole antibodies or fragments of the antibodies comprising the antigen-binding domain of the anti-VEGFV product antibodies, e.g. antibodies without the Fc portion, single chain antibodies, fragments consisting of essentially only the variable, antigen-binding domain of the antibody, etc.

"Activator"—as used herein, refers to a molecule which mimics the effect of the natural VEGFV product or at times even increases or prolongs the duration of the biological activity of said product, as compared to that induced by the natural product. The mechanism may be by binding to the VEGFV receptor, by prolonging the lifetime of the VEGFV, by increasing the activity of the VEGFV on its target (vascular endothelial cells), by increasing the affinity of VEGFV to its receptor, etc. Activators may be polypeptides, nucleic acids, carbohydrates, lipids, or derivatives thereof, or any other molecules which can bind to and activate the VEGFV product.

"Deactivator" or ("Inhibitor")—refers to a molecule which modulates the activity of the VEGFV product in an opposite manner to that of the activator, by decreasing or shortening the duration of the biological activity of the VEGFV product. This may be done by blocking the binding of the VEGFV to its receptor (competitive or non-competitive inhibition), by causing rapid degradation of the VEGFV, etc. Deactivators may be polypeptides, nucleic acids, carbohydrates, lipids, or derivatives thereof, or any other molecules which bind to and modulate the activity of said product.

"Treating a disease"—refers to administering a therapeutic substance effective to ameliorate symptoms associated with a disease, to lessen the severity or cure the disease, or to prevent the disease from occurring.

"Detection"—refers to a method of detection of a disease. This term may refer to detection of a predisposition to a disease.

"Probe"—the VEGFV nucleic acid sequence, or a sequence complementary therewith, when used to detect presence of other similar sequences in a sample. The detection is carried out by identification of hybridization complexes between the probe and the assayed sequence. The probe may be attached to a solid support or to a detectable label.

SUMMARY OF THE INVENTION

The present invention is based on the surprising finding that there exist in humans a novel variant of the VEGF protein, having 141 amino acid (114 amino acids of the mature protein without the signal peptide) than the known VEGF. The nucleic sequence coding for this variant was identified as being from the same locus as the known VEGF and thus it was concluded that the variant is not encoded from a different gene than the known VEGF, but is the result of alternative splicing of the known VEGF.

Thus the present invention provides by its first aspect, a novel isolated nucleic acid molecule comprising or consisting of the coding sequence SEQ ID NO: 1, fragments of said coding sequence having at least 20 nucleic acids, or a molecule comprising a sequence having at least 70%, preferably 80%, and most preferably 90% identity to SEQ ID NO:1.

The present invention further provides a protein or polypeptide comprising or consisting of an amino acid sequence encoded by any of the above nucleic acid sequences, termed herein "VEGFV product", for example, an amino acid sequence having the sequence as depicted in SEQ ID NO: 2, fragments of the above amino acid sequence having a length of at least 10 amino acids, as well as homologs of the amino acid sequences SEQ ID NO.:2 in which one or more of the amino acid residues has been substituted (by conservative or non-conservative substitution) added, deleted, or chemically modified.

The present invention further provides nucleic acid molecule comprising or consisting of a sequence which encodes the above amino acid sequences, (including the fragments and analogs of the amino acid sequences). Due to the degenerative nature of the genetic code, a plurality of alternative nucleic acid sequences, beyond SEQ ID NO:1, can code for the amino acid sequence of the invention. Those alternative nucleic acid sequences which code for the same amino acid sequences codes by the sequence SEQ ID NO: 1 are also an aspect of the of the present invention.

The present invention further provides expression vectors and cloning vectors comprising any of the above nucleic acid sequences, as well as host cells transfected by said vectors.

The present invention still further provides pharmaceutical compositions comprising, as an active ingredient, said nucleic acid molecules, said expression vectors, or said protein or polypeptide.

These pharmaceutical compositions are suitable for the treatment of diseases and pathological conditions, which can be ameliorated or cured by raising the level of the VEGFV product.

By a second aspect, the present invention provides a nucleic acid molecule comprising or consisting of a non-coding sequence which is complementary to that of SEQ ID NO:1, or complementary to a sequence having at least 70% identity to said sequence or a fragment of said two sequences. The complementary sequence may be a DNA sequence which hybridizes with the SEQ of ID NO:1 or hybridizes to a portion of that sequence having a length sufficient to inhibit the transcription of the complementary sequence. The complementary sequence may be a DNA sequence which can be transcribed into an mRNA being an antisense to the mRNA transcribed from SEQ ID NO:1 or into an mRNA which is an antisense to a fragment of the mRNA transcribed from SEQ ID NO:1 which has a length sufficient to hybridize with the mRNA transcribed from SEQ ID NO: 1, so as to inhibit its translation. The complementary sequence may also be the mRNA or the fragment of the mRNA itself.

The nucleic acids of the second aspect of the invention may be used for therapeutic or diagnostic applications for example for detection of the expression of VEGFV. The proportion of expression of the VEGF variant of the present invention as compared to the known VEGF variants may be indicative to a variety of physiological or pathological conditions.

The present invention also provides expression vectors comprising any one of the above defined complementary nucleic acid sequences and host cells transfected with said nucleic acid sequences or vectors, being complementary to those specified in the first aspect of the invention.

The invention also provides anti-VEGFV product antibodies, namely antibodies directed against the VEGFV product which specifically bind to said VEGFV product. Said antibodies are useful both for diagnostic and therapeutic purposes. For example said antibody may be as an active ingredient in a pharmaceutical composition as will be explained below.

The present invention also provides pharmaceutical compositions comprising, as an active ingredient, the nucleic acid molecules which comprise or consist of said complementary sequences, or of a vector comprising said complementary sequences. The pharmaceutical composition thus provides pharmaceutical compositions comprising, as an active ingredient, said anti-VEGFV product antibodies.

The pharmaceutical compositions comprising said anti-VEGFV product antibodies or the nucleic acid molecule comprising said complementary sequence, are suitable for the treatment of diseases and pathological conditions where a therapeutically beneficial effect may be achieved by neutralizing the VEGFV or decreasing the amount of the VEGFV product or blocking its binding to the receptor, for example, by the neutralizing effect of the antibodies, or by the decrease of the effect of the antisense mRNA in decreasing expression level of the VEGFV product.

According to the third aspect of the invention the present invention provides methods for detecting the level of the transcript (mRNA) of said VEGFV product in a body fluid sample, or in a specific tissue sample, for example by use of probes comprising or consisting of said coding sequences; as well as methods for detecting levels of expression of said product in tissue, e.g. by the use of antibodies capable of specifically reacting with the above amino acid sequences. Detection of the level of the expression of the VEGF variant of the invention in particular as compared to that of the known VEGF variants may be indicative of a plurality of physiological or pathological conditions.

The method, according to this latter aspect, for detection of a nucleic acid sequence which encodes the VEGFV product in a biological sample, comprises the steps of:

(a) providing a probe comprising at least one of the nucleic acid sequence defined above;

(b) contacting the biological sample with said probe under conditions allowing hybridization of nucleic acid sequences thereby enabling formation of hybridization complexes;

(c) detecting hybridization complexes, wherein the presence of the complex indicates the presence of nucleic acid sequence encoding the VEGFV product in the biological sample.

By a preferred embodiment the probe is part of a nucleic acid chip used for detection purposes, i.e. the probe is a part of an array of probes each present in a known location on a solid support.

The nucleic acid sequence used in the above method may be a DNA sequence an RNA sequence, etc; it may be a coding or a sequence or a sequence complementary thereto (for respective detection of RNA transcripts or coding-DNA sequences). By quantization of the level of hybridization complexes and calibrating the quantified results it is possible also to detect the level of the transcript in the sample.

Methods for detecting mutations in the region coding for the VEGFV product are also provided, which may be methods carried-out in a binary fashion, namely merely detecting whether there is any mismatches between the normal VEGFV nucleic acid sequence and the one present in the sample, or carried-out by specifically detecting the nature and location of the mutation.

The present invention also concerns a method for detecting VEGFV product in a biological sample, comprising the steps of:

(a) contacting with said biological sample the antibody of the invention, thereby forming an antibody-antigen complex; and (b) detecting said antibody-antigen complex wherein the presence of said antibody-antigen complex correlates with the presence of VEGFV product in said biological sample.

By yet another aspect the invention also provides a method for identifying candidate compounds capable of binding to the VEGFV product and modulating its activity (being either activators or deactivators). The method includes:

(i) providing a protein or polypeptide comprising an amino acid sequence substantially as depicted in SEQ ID NO: 2, or a fragment of such a sequence;

(ii) contacting a candidate compound with said amino acid sequence;

(iii) measuring the physiological effect of said candidate compound on the activity of the amino acid sequences and selecting those compounds which show a significant effect on said physiological activity.

The activity of the amino acid which should be changed by the modulator (being either the activator or deactivator) may be for example the binding of the VEGFV product to its native receptor, effect on the modulation in the effect of VEGFV on vascular endothelial cells, etc. Any modulator which changes such an activity has an intersecting potential.

The present invention also concerns compounds identified by the above methods described above, which compound may either be an activator of the serotonin-receptor like product or a deactivator thereof.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

EXAMPLE I

VEGFV—Nucleic Acid Sequence

Figure 1:
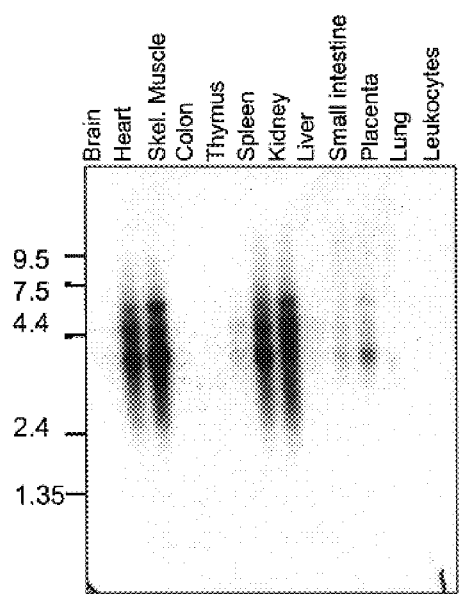
FIGS. 1 and 2 show a Northern blot analysis of RNA obtained from various tissues and tested with a probe specific for known VEGFs but lacking the VEGF variant of the invention (termed "VEGF") (left), as well as a unique probe from the 3'UTR region of VEGF-114 (right).
Figure 1:
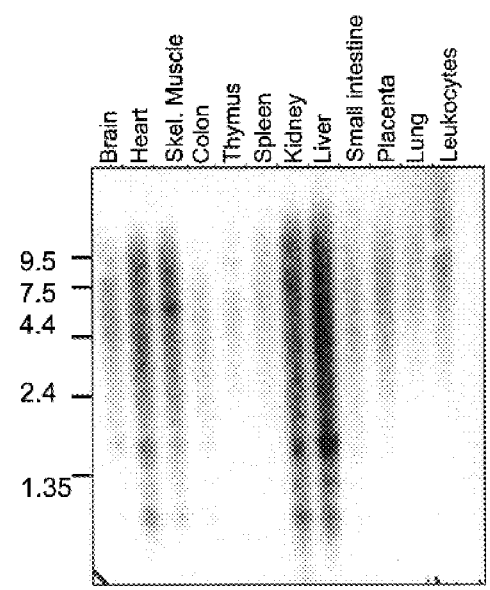
Figure 2:
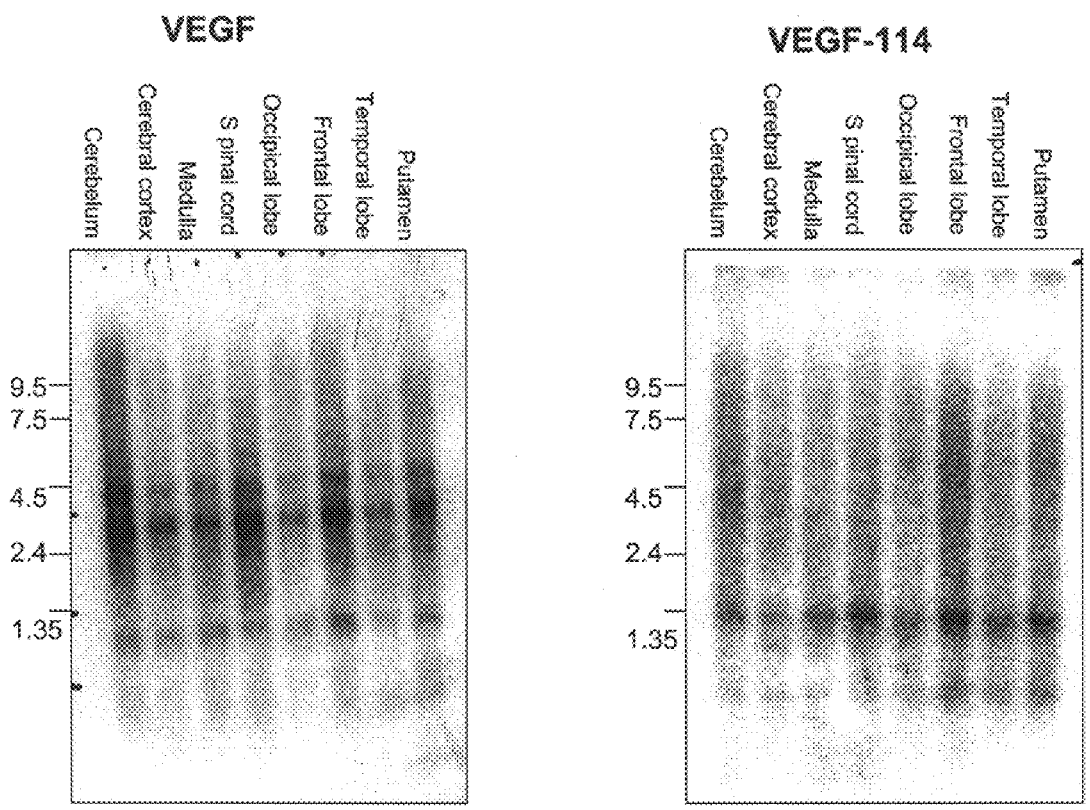

The nucleic acid sequences of the invention include nucleic acid sequences which encode VEGFV product and fragments and analogs thereof. The nucleic acid sequences may alternatively be sequences complementary to the above coding sequence, or to a region of said coding sequence. The length of the complementary sequence is sufficient to avoid the expression of the coding sequence. The nucleic acid sequences may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand. The nucleic acid sequences may also both include dNTPs, rNTPs as well as non naturally occurring sequences. The sequence may also be a part of a hybrid between an amino acid sequence and a nucleic acid sequence.

In a general embodiment, the nucleic acid sequence has at least 70%, preferably 80% or 90% sequence identity with the sequence identified as SEQ ID NO:1.

The nucleic acid sequences may include the coding sequence by itself. By another alternative the coding region may be in combination with additional coding sequences, such as those coding for fusion protein or signal peptides, in combination with non-coding sequences, such as introns and control elements, promoter and terminator elements or 5' and/or 3' untranslated regions, effective for expression of the coding sequence in a suitable host, and/or in a vector or host environment in which the VEGFV nucleic acid sequence is introduced as a heterologous sequence.

The nucleic acid sequences of the present invention may also have the product coding sequence fused in-frame to a marker sequence which allows for purification of the VEGFV product. The marker sequence may be, for example, a hexahistidine tag to provide for purification of the mature polypeptide fused to the marker in the case of a bacterial host, or, the marker sequence may be a hemagglutinin (HA) tag when a mammalian host, e.g. COS-7 cells, is used. The HA tag corresponds to an epitope derived from the influenza hemagglutinin protein (Wilson, I., et al. *Cell* 37:767 (1984)).

Also included in the scope of the invention are fragments also referred to herein as oligonucleotides, typically having at least 20 bases, preferably 20–30 bases corresponding to a region of the coding-sequence nucleic acid sequence. The fragments may be used as probes, primers, and when complementary also as antisense agents, and the like, according to known methods.

As indicated above, the nucleic acid sequence may be substantially a depicted in SEQ ID NO:1 or fragments thereof or sequences having at least 70%, preferably 70–80%, most preferably 90% identity to the above sequence. Alternatively, due to the degenerative nature of the genetic code, the sequence may be a sequence coding the amino acid sequence of SEQ ID NO:2, or fragments or analogs of said amino acid sequence.

A. Preparation of Nucleic Acid Sequences

The nucleic acid sequences may be obtained by screening cDNA libraries using oligonucleotide probes which can hybridize to or PCR-amplify nucleic acid sequences which encode the VEGFV products disclosed above. cDNA libraries prepared from a variety of tissues are commercially available and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel F M et al. (1989) Current Protocols in Molecular Biology, John Wiley & Sons, New York, N.Y.

The nucleic acid sequences may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the Marathon RACE kit (Clontech, Cat. #K1802-1).

Alternatively, the technique of "restriction-site" PCR (Gobinda et al. *PCR Methods Applic.* 2:318–22, (1993)), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, T. et al., *Nucleic Acids Res.* 16:8186, (1988)). The primers may be designed using OLOGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom, M. et al., *PCR Methods Applic.* 1:111–19, (1991)) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J. D., et al., *Nucleic Acids Res.*, 19:3055–60, (1991)). Additionally, one can use PCR, nested primers and PromoterFinder™ libraries to "walk in" genomic DNA (PromoterFinder™; Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes.

A randomly primed library may be particularly useful if an oligo d(T) library does not yield a full-length cDNA. Genomic libraries are useful for extension into the 5' non-translated regulatory region.

The nucleic acid sequences and oligonucleotides of the invention can also be prepared by solid-phase methods, according to known synthetic methods. Typically, fragments of up to about 100 bases are individually synthesized, then joined to form continuous sequences up to several hundred bases.

B. Use of VEGFV nucleic acid sequence for the production of VEGFV products

In accordance with the present invention, nucleic acid sequences specified above may be used as recombinant DNA molecules that direct the expression of VEGFV products.

As will be understood by those of skill in the art, it may be advantageous to produce VEGFV product-encoding nucleotide sequences possessing codons other than those which appear in SEQ ID NO:1 which are those which naturally occur in the human genome. Codons preferred by a particular prokaryotic or eukaryotic host (Murray, E. et al. *Nuc Acids Res.*, 17:477–508, (1989)) can be selected, for example, to increase the rate of VEGFV product expression or to produce recombinant RNA transcripts having desirable properties, such as a longer half-life, than transcripts produced from naturally occurring sequence.

The nucleic acid sequences of the present invention can be engineered in order to alter a VEGFV product coding sequence for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, to produce splice variants, etc.

The present invention also includes recombinant constructs comprising one or more of the sequences as broadly described above. The constructs comprise a vector, such as a plasmid or viral vector, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells which are genetically engineered with vectors of the invention, and the production of the product of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the expression of the VEGFV nucleic acid sequence. The culture conditions, such as temperature, pH and the like, are those previously used with the host cell selected for expression, and will be apparent to those skilled in the art.

The nucleic acid sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the *E. coli* lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli*, Streptomyces, *Salmonella typhimarium*; fungal cells, such as yeast; insect cells such as Drosophila and Spodoptera Sf9; animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed.

In bacterial systems, a number of expression vectors may be selected depending upon the use intended for the VEGFV product. For example, when large quantities of VEGFV product are needed for the induction of antibodies, vectors which direct high level expression of fusion proteins that are readily purified may be desirable. Such vectors include, but are not limited to, multifunctional *E. coli* cloning and expression vectors such as Bluescript(R) (Stratagene), in which the VEGFV polypeptide coding sequence may be ligated into the vector in-frame with sequences for the amino-terminal Met and the subsequent 7 residues of beta-galactosidase so that a hybrid protein is produced; pIN vectors (Van Heeke & Schuster *J. Biol. Chem.* 264:5503–5509, (1989)); pET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al., (*Methods in Enzymology* 153:516–544, (1987)).

In cases where plant expression vectors are used, the expression of a sequence encoding VEGFV product may be driven by any of a number of promoters. For example, viral promoters such as the 35S and 19S promoters of CaMV (Brisson et al., *Nature* 310:511–514, (1984)) may be used alone or in combination with the omega leader sequence from TMV (Takamatsu et al., *EMBO J.*, 6:307–311, (1987)). Alternatively, plant promoters such as the small subunit of RUBISCO (Coruzzi et al., *EMBO J.* 3:1671–1680, (1984); Broglie et al., *Science* 224:838–843, (1984)); or heat shock promoters (Winter J and Sinibaldi R. M., *Results Probl. Cell Differ.*, 17:85–105, (1991)) may be used. These constructs can be introduced into plant cells by direct DNA transformation or pathogen-mediated transfection. For reviews of such techniques, see Hobbs S. or Murry L. E. (1992) in McGraw Hill Yearbook of Science and Technology, McGraw Hill, New York, N.Y., pp 191–196; or Weissbach and Weissbach (1988) *Methods for Plant Molecular Biology*, Academic Press, New York, N.Y., pp 421–463.

VEGFV product may also be expressed in an insect system. In one such system, Autographa californica nuclear polyhedrosis virus (AcNPV) is used as a vector to express foreign genes in *Spodoptera frugiperda* cells or in Trichoplusia larvae. The VEGFV product coding sequence may be cloned into a nonessential region of the virus, such as the polyhedrin gene, and placed under control of the polyhedrin promoter. Successful insertion of VEGFV coding sequence will render the polyhedrin gene inactive and produce recombinant virus lacking coat protein coat. The recombinant viruses are then used to infect *S. frugiperda* cells or Trichoplusia larvae in which VEGFV protein is expressed (Smith et al., *J. Virol.* 46:584, (1983); Engelhard, E. K. et al., *Proc. Nat. Acad. Sci.* 91:3224–7, (1994)).

In mammalian host cells, a number of viral-based expression systems may be utilized. In cases where an adenovirus is used as an expression vector, a VEGFV product coding sequence may be ligated into an adenovirus transcription/translation complex consisting of the late promoter and tripartite leader sequence. Insertion in a nonessential E1 or E3 region of the viral genome will result in a viable virus capable of expressing VEGFV protein in infected host cells (Logan and Shenk, *Proc. Natl. Acad. Sci.* 81:3655–59, (1984). In addition, transcription enhancers, such as the Rous sarcoma virus (RSV) enhancer, may be used to increase expression in mammalian host cells.

Specific initiation signals may also be required for efficient translation of a VEGFV protein coding sequence. These signals include the ATG initiation codon and adjacent sequences. In cases where VEGFV product coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., (1994) *Results Probl. Cell Differ.*, 20:125–62, (1994); Bittner et al., *Methods in Enzymol* 153:516–544, (1987)).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre-pro" form of the protein may also be important for correct insertion, folding and/or function. Different host cells such as CHO, HeLa, MDCK, 293, W138, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express VEGFV product may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M., et al., *Cell* 11:223–32, (1977)) and adenine phosphoribosyltransferase (Lowy J., et al., *Cell* 22:817–23, (1980)) genes which can be employed in tk- or aprt- cells, respectively. Also, antimetabolite, antibiotic or herbicide resistance can be used as the basis for selection; for example, dhfr which confers resistance to methotrexate (Wigler M., et al., *Proc. Natl. Acad. Sci.* 77:3567–70, (1980)); npt, which confers resistance to the aminoglycosides neomycin and G-418 (Colbere-Garapin, F. et al., *J. Mol. Biol.,* 150:1–14, (1981)) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan, *Proc. Natl. Acad. Sci.* 85:8047–51, (1988)). The use of visible markers has gained popularity with such markers as anthocyanins, beta-glucuronidase and its substrate, GUS, and luciferase and its substrates, luciferin and ATP, being widely used not only to identify transformants, but also to quantify the amount of transient or stable protein expression attributable to a specific vector system (Rhodes, C. A. et. al., *Methods Mol. Biol.,* 55:121–131, (1995)).

Host cells transformed with a nucleotide sequence encoding VEGFV product may be cultured under conditions suitable for the expression and recovery of the encoded protein from cell culture. The product produced by a recombinant cell may be secreted or contained intracellularly depending on the sequence and/or the vector used. As will be understood by those of skill in the art, expression vectors containing nucleic acid sequences encoding VEGFV product can be designed with signal sequences which direct secretion of VEGFV product through a prokaryotic or eukaryotic cell membrane.

VEGFV product may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and VEGFV protein is useful to facilitate purification. One such expression vector provides for expression of a fusion protein compromising a VEGFV polypeptide fused to a polyhistidine region separated by an enterokinase cleavage site. The histidine residues facilitate purification on IMIAC (immobilized metal ion affinity chromatography, as described in Porath, et al., *Protein Expression and Purification,* 3:263–281, (1992)) while the enterokinase cleavage site provides a means for isolating VEGFV polypeptide from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by absorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an addition period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

The VEGFV products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

C. Diagnostic applications utilizing nucleic acid sequences

The nucleic acid sequences of the present invention may be used for a variety of diagnostic purposes. The nucleic acid sequences may be used to detect and quantitate expression of VEGFV in patient's cells, e.g. biopsied tissues, by detecting the presence of mRNA coding for VEGFV product. Alternatively, the assay may be used to detect soluble VEGFV in the serum or blood. This assay typically involves obtaining total mRNA from the tissue or serum and contacting the mRNA with a nucleic acid probe. The probe is a nucleic acid molecule of at least 20 nucleotides, preferably 20–30 nucleotides, capable of specifically hybridizing with a sequence included within the sequence of a nucleic acid molecule encoding VEGFV under hybridizing conditions, detecting the presence of mRNA hybridized to the probe, and thereby detecting the expression of VEGFV. This assay can be used to distinguish between absence, presence, and excess expression of VEGFV product and to monitor levels of VEGFV expression during therapeutic intervention.

The invention also contemplates the use of the nucleic acid sequences as a diagnostic for diseases resulting from inherited defective VEGFV sequences, or diseases in which the purpose of the amount of the known VEGF to the novel VEGF variant of the invention is altered. These sequences can be detected by comparing the sequences of the defective (i.e., mutant) VEGFV coding region with that of a normal coding region. Association of the sequence coding for mutant VEGFV product with abnormal VEGFV product activity may be verified. In addition, sequences encoding mutant VEGFV products can be inserted into a suitable vector for expression in a functional assay system (e.g., colorimetric assay, complementation experiments in a VEGFV protein deficient strain of HEK293 cells) as yet another means to verify or identify mutations. Once mutant genes have been identified, one can then screen populations of interest for carriers of the mutant gene.

Individuals carrying mutations in the nucleic acid sequence of the present invention may be detected at the DNA level by a variety of techniques. Nucleic acids used for diagnosis may be obtained from a patient's cells, including but not limited to such as from blood, urine, saliva, placenta, tissue biopsy and autopsy material. Genomic DNA may be used directly for detection or may be amplified enzymatically by using PCR (Saiki, et al., *Nature* 324:163–166, (1986)) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and Sl protection or the chemical cleavage method (e.g. Cotton, et al *Proc. Natl. Acad. Sci.* USA, 85:4397–4401, (1985)), or by differences in melting temperatures. *"Molecular beacons"* (Kostrikis L. G. et al., Science 279:1228–1229, (1998)), hairpin-shaped, single-stranded synthetic oligonucleotides containing probe sequences which are complementary to the nucleic acid of the present invention, may also be used to detect point mutations or other sequence changes as well as monitor expression levels of VEGFV product. Such diagnostics would be particularly useful for prenatal testing.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the VEGFV product coding sequence are oligonucleotide array methods based on sequencing by hybridization (SBH), as described, for example, in U.S. Pat. No. 5,547,839. In a typical method, the DNA target analyte is hybridized with an array of oligonucleotides formed on a microchip. The sequence of the target can then be "read" from the pattern of target binding to the array.

RNA was obtained from the following tissues: putamen, temporal lobe, frontal lobe, occipital lobe, spinal cord, medulla, cerebral cortex, brain, heart, skeletal muscle, colon, thymus, spleen, kidney, liver, small intestine, placenta lung and leukocytes and was hybridized either with an VEGF probe or with a probe from the unique 3' UTR region of the VEGF-V of the invention. The results are shown in FIGS. 1 and 2. As can be seen the new VEGF-V probe of the invention shows, in general, similar hybridization patterns to those of native VEGF.

D. Gene mapping utilizing nucleic acid sequences

The nucleic acid sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping DNAs to chromosomes according to the present invention is an important first step in correlating those sequences with genes associated with disease.

Briefly, sequences can be mapped to chromosomes by preparing PCR primers (preferably 20–30 bp) from the VEGFV cDNA. Computer analysis of the 3' untranslated region is used to rapidly select primers that do not span more than one exon in the genomic DNA, which would complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids or using instead radiation hybrids are rapid procedures for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselected by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., *Human Chromosomes: a Manual of Basic Techniques,* (1988) Pergamon Press, New York.

Once a sequence has been mapped to a precise chromosomal location, the physical position of the sequence on the chromosome can be correlated with genetic map data. Such data are found, for example, in the OMIM database (Center for Medical Genetics, Johns Hopkins University, Baltimore, Md. and National Center for Biotechnology Information, National Library of Medicine, Bethesda, Md.). The OMIM gene map presents the cytogenetic map location of disease genes and other expressed genes. The OMIM database provides information on diseases associated with the chromosomal location. Such associations include the results of linkage analysis mapped to this interval, and the correlation of translocations and other chromosomal aberrations in this area with the advent of polygenic diseases, such as cancer, in general and prostate cancer in particular.

E. Therapeutic applications of nucleic acid sequences

Nucleic acid sequences of the invention may also be used for therapeutic purposes. Turning first to the second aspect of the invention (i.e. inhibition of expression of VEGFV), expression of VEGFV product may be modulated through antisense technology, which controls gene expression through hybridization of complementary nucleic acid sequences, i.e. antisense DNA or RNA, to the control, 5' or regulatory regions of the gene encoding VEGFV product. For example, the 5' coding portion of the nucleic acid sequence sequence which codes for the product of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the nucleic acid sequence involved in transcription (Lee et al., *Nucl. Acids, Res.,* 6:3073, (1979); Cooney et al., Science 241:456, (1988); and Dervan et al., *Science* 251:1360, (1991)), thereby preventing transcription and the production of the VEGFV products. An antisense RNA oligonucleotide hybridizes to the mRNA in vivo and blocks translation of the mRNA molecule into the VEGFV products (Okano *J. Neurochem.* 56:560, (1991)). The antisense constructs can be delivered to cells be procedures known in the art such that the antisense RNA or DNA may be expressed in vivo. The antisense may be antisense mRNA or DNA sequence capable of coding such antisense mRNA. The antisense mRNA or the DNA coding thereof can be complementary to the full sequence of nucleic acid sequences coding to the VEGFV protein or to a fragment of such a sequence which is sufficient to inhibit production of a protein product.

Turning now to the first aspect of the invention, i.e. expression of VEGFV, expression of VEGFV product may be increased by providing coding sequences for coding for said product under the control of suitable control elements ending its expression in the desired host.

The nucleic acid sequences of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The products of the invention as well as any activators and deactivators compounds (see below) which are polypeptides, may also be employed in accordance with the present invention by expression of such polypeptides in vivo, which is often referred to as "gene therapy." Cells from a patient may be engineered with a nucleic acid sequence (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a product of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+envAm12, and DAN cell lines as described in Miller (*Human Gene Therapy,* Vol. 1, pg. 5–14, (1990)). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The tranduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The genes introduced into cells may be placed under the control of inducible promoters, such as the radiation-inducible Egr-1 promoter, (Maceri, H. J., et al., *Cancer Res.,* 56(19):4311 (1996)), to stimulate VEGFV production or antisense inhibition in response to radiation, eg., radiation therapy for treating tumors.

EXAMPLE II

VEGFV Product

The substantially purified VEGFV product of the invention has been defined above as the product coded from the nucleic acid sequence of the invention. Preferably the amino acid sequence is an amino acid sequence having at least 70%, preferably at least 80% or 90% identity to the sequence identified as SEQ ID NO:2. The protein or polypeptide may be in mature and/or modified form, also as defined above. Also contemplated are protein fragments having at least 10 contiguous amino acid residues, preferably at least 10–20 residues, derived from the VEGFV product.

The sequence variations are preferably those that are considered conserved substitutions, as defined above. Thus, for example, a protein with a sequence having at least 80% sequence identity with the protein identified as SEQ ID NO:2, preferably by utilizing conserved substitutions as defined above is also part of the invention. In a more specific embodiment, the protein has or contains the sequence identified SEQ ID NO:2. The VEGFV product may be (i) one in which one or more of the amino acid residues in a sequence listed above are substituted with a conserved or non-conserved amino acid residue (preferably a conserved amino acid residue), or (ii) one in which one or more of the amino acid residues includes a substituent group, or (iii) one in which the VEGFV product is fused with another compound, such as a compound to increase the half-life of the protein (for example, polyethylene glycol (PEG)), or a moiety which serves as targeting means to direct the protein to its target tissue or target cell population (such as an antibody), or (iv) one in which additional amino acids are fused to the VEGFV product. Such fragments, variants and derivatives are deemed to be within the scope of those skilled in the art from the teachings herein.

A. Preparation of VEGFV product

Recombinant methods for producing and isolating the VEGFV product, and fragments of the protein are described above.

In addition to recombinant production, fragments and portions of VEGFV product may be produced by direct peptide synthesis using solid-phase techniques (cf. Stewart et al., (1969) Solid-Phase Peptide Synthesis, W H Freeman Co, San Francisco; Merrifield J., *J. Am. Chem. Soc.,* 85:2149–2154, (1963)). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Fragments of VEGFV product may be chemically synthesized separately and combined using chemical methods to produce the full length molecule.

Figure 3:
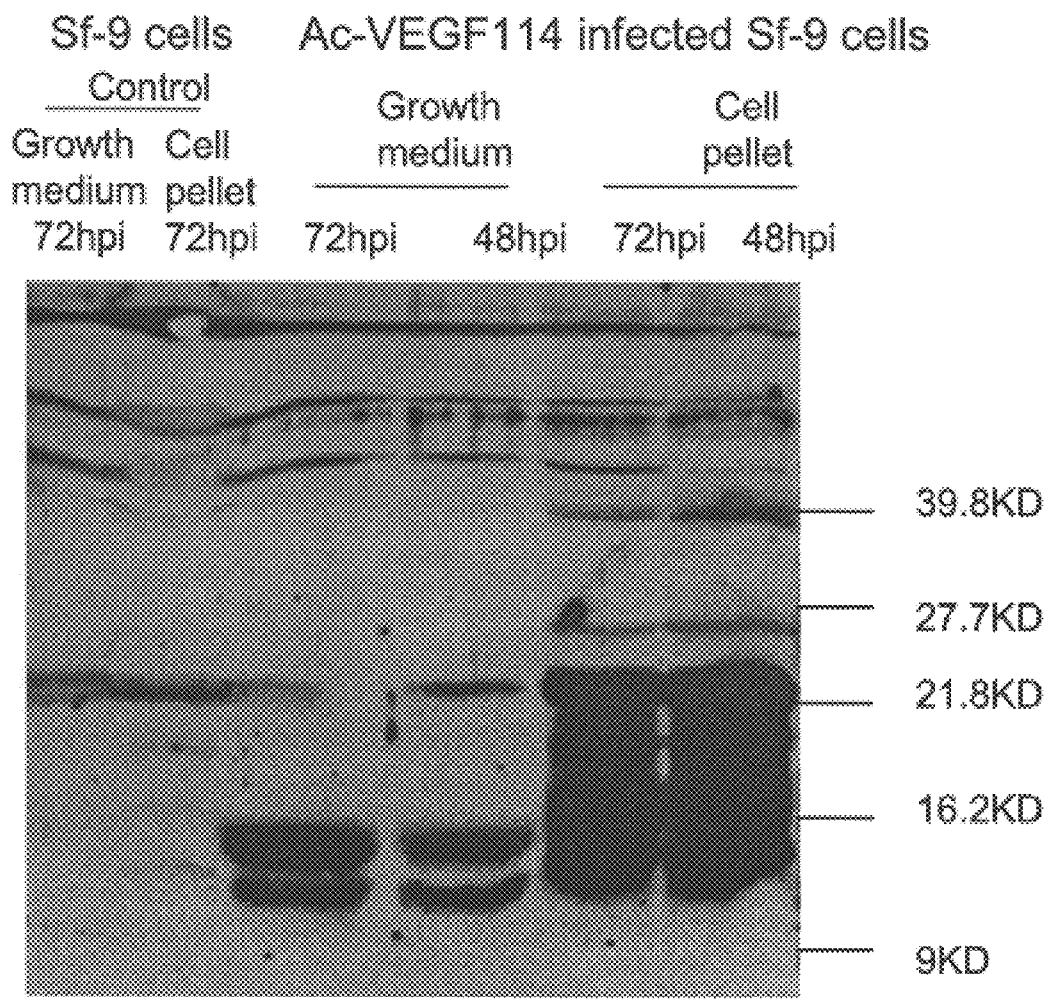
FIG. 3 shows a Western blot analysis of Ac-VEGF-114 infected insect cells using the VEGF (147) polyclonal antibody (Santa Cruz Biotechnology).

The VEGF-V of the invention was cloned into the Back to Back Baculovirus Expression System (Invitrogen). Briefly, the gene was inserted into the pFastBackHTal transfer vector (including a 6xHis tag on its 5'). The resulting transfer vector (pFBHTal-VEGF) was confirmed for the correct insertion by sequencing. pFBHTal-VEGF was then transformed into DH10Bac competent cells (containing the ACNPV viral genome in the form of bacmid DNA). White colonies obtained from the transformation were verified by PCR with gene specific and viral specific primers for the VEGF insertion into the viral genome under the polh promoter. The bacmid DNA was extracted from a positive colony and transfected into insect cells (Sf-9). Viral particles were collected and used for two consecutive infections in order to amplify the viral stock. The viral particles collected from the second infection was used for infection of Sf-9 cells in suspension. Samples were collected at 48 and 72 hours post infection (hpi) and centrifuged in order to verify protein expression in cells pellet and its secretion into the medium. The different samples were subjected for western blotting using the VEGF(147) polyclonal antibody (Santa Cruz Biotechnology), and the results are shown in FIG. 3.

As can be seen the medium contains two bands of size around 11KD and 15KD. The 15KD band corresponds for the 6XHis-VEGF translation starting at the His tag AUG and the 11KD band corresponds for the VEGF translation starting from the VEGF gene AUG.

B. Therapeutic uses and compositions utilizing the VEGFV product

The VEGFV product of the invention is generally useful in treating diseases and disorders which are characterized by a lower than normal level of VEGFV expression, and or diseases which can be cured or ameliorated by raising the level of the VEGFV product, even if the level is normal.

VEGFV products or fragments may be administered by any of a number of routes and methods designed to provide a consistent and predictable concentration of compound at the target organ or tissue. The product-containing compositions may be administered alone or in combination with other agents, such as stabilizing compounds, and/or in combination with other pharmaceutical agents such as drugs or hormones.

VEGFV product-containing compositions may be administered by a number of routes including, but not limited to oral, intravenous, intramuscular, transdermal, subcutaneous, topical, sublingual, or rectal means as well as by nasal application. VEGFV product-containing compositions may also be administered via liposomes. Such administration routes and appropriate formulations are generally known to those of skill in the art.

The product can be given via intravenous or intraperitoneal injection. Similarly, the product may be injected to other localized regions of the body. The product may also be administered via nasal insufflation. Enteral administration is also possible. For such administration, the product should be formulated into an appropriate capsule or elixir for oral administration, or into a suppository for rectal administration.

The foregoing exemplary administration modes will likely require that the product be formulated into an appropriate carrier, including ointments, gels, suppositories. Appropriate formulations are well known to persons skilled in the art.

Dosage of the product will vary, depending upon the potency and therapeutic index of the particular polypeptide selected.

A therapeutic composition for use in the treatment method can include the product in a sterile injectable solution, the polypeptide in an oral delivery vehicle, the product in an aerosol suitable for nasal administration, or the product in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The product of the invention may also be used to modulate endothelial differentiation and proliferation as well as to modulate apoptosis either ex vivo or in vitro, for example, in cell cultures.

EXAMPLE III

Screening Methods for Activators and Deactivators (Inhibitors)

The present invention also includes an assay for identifying molecules, such as synthetic drugs, antibodies, peptides, or other molecules, which have a modulating effect on the activity of the VEGFV product, e.g. activators or deactivators of the VEGFV product of the present invention. Such an assay comprises the steps of providing an VEGFV product encoded by the nucleic acid sequences of the present invention, contacting the VEGFV protein with one or more candidate molecules to determine the candidate molecules modulating effect on the activity of the VEGFV product, and selecting from the molecules a candidate's molecule capable of modulating VEGFV product physiological activity.

VEGFV product, its catalytic or immunogenic fragments or oligopeptides thereof, can be used for screening therapeutic compounds in any of a variety of drug screening techniques. The fragment employed in such a test may be free in solution, affixed to a solid support, borne on a cell membrane or located intracellularly. The formation of binding complexes, between VEGFV product and the agent being tested, may be measured. Alternatively, the activator or deactivator may work by serving as agonist or antagonist, respectively, of the VEGFV receptor and their effect may be determined in connection with the receptor.

Another technique for drug screening which may be used provided for high throughput screening of compounds having suitable binding affinity to the VEGFV product is described in detail by Geysen in PCT Application WO 84/03564, published on Sep. 13, 1984. In summary, large numbers of different small peptide test compounds are synthesized on a solid substrate, such as plastic pins or some other surface. The peptide test compounds are reacted with the full VEGFV product or with fragments of VEGFV product and washed. Bound VEGFV product is then detected by methods well known in the art. Substantially purified VEGFV product can also be coated directly onto plates for use in the aforementioned drug screening techniques. Alternatively, non-neutralizing antibodies can be used to capture the peptide and immobilize it on a solid support.

Antibodies to the VEGFV product, as described in Example IV below, may also be used in screening assays according to methods well known in the art. For example, a "sandwich" assay may be performed, in which an anti-VEGFV antibody is affixed to a solid surface such as a microtiter plate and VEGFV product is added. Such an assay can be used to capture compounds which bind to the VEGFV product. Alternatively, such an assay may be used to measure the ability of compounds to influence with the binding of VEGFV product to the VEGFV receptor, and then select those compounds which effect the binding.

EXAMPLE IV

Anti-VEGFV Antibodies

A. Synthesis

In still another aspect of the invention, the purified VEGFV product is used to produce anti-VEGFV antibodies which have diagnostic and therapeutic uses related to the activity, distribution, and expression of the VEGFV product, in particular therapeutic applications in inhibiting the effect of the VEGFV on vascular endothelial cells.

Antibodies to VEGFV product may be generated by methods well known in the art. Such antibodies may include, but are not limited to, polyclonal, monoclonal, chimeric, humanized, single chain, Fab fragments and fragments produced by an Fab expression library. Antibodies, i.e., those which inhibit dimer formation, are especially preferred for therapeutic use.

A fragment VEGFV product for antibody induction does not require biological activity but have to feature immunological activity; however, the protein fragment or oligopeptide must be antigenic. Peptides used to induce specific antibodies may have an amino acid sequence consisting of at least five amino acids, preferably at least 10 amino acids of the sequences specified in SEQ ID NO: 2. Preferably they should mimic a portion of the amino acid sequence of the natural protein and may contain the entire amino acid sequence of a small, naturally occurring molecule. Short stretches of VEGFV protein amino acids may be fused with those of another protein such as keyhole limpet hemocyanin and antibody produced against the chimeric molecule. Procedures well known in the art can be used for the production of antibodies to VEGFV product.

For the production of antibodies, various hosts including goats, rabbits, rats, mice, etc may be immunized by injection with VEGFV product or any portion, fragment or oligopeptide which retains immunogenic properties. Depending on the host species, various adjuvants may be used to increase immunological response. Such adjuvants include but are not limited to Freund's mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to VEGFV protein may be prepared using any technique which provides for the production of antibody molecules by continuous cell lines in culture. These include but are not limited to the hybridoma technique originally described by Koehler and Milstein (*Nature* 256:495–497, (1975)), the human B-cell hybridoma technique (Kosbor et al., *Immunol. Today* 4:72, (1983); Cote et al., *Proc. Natl. Acad. Sci.* 80:2026–2030, (1983)) and the EBV-hybridoma technique (Cole, et al., *Mol. Cell Biol.* 62:109–120, (1984)).

Techniques developed for the production of "chimeric antibodies", the splicing of mouse antibody genes to human antibody genes to obtain a molecule with appropriate antigen specificity and biological activity can also be used (Morrison et al., *Proc. Natl. Acad. Sci.* 81:6851–6855, (1984); Neuberger et al., *Nature* 312:604–608, (1984); Takeda et al., *Nature* 314:452–454, (1985)). Alternatively, techniques described for the production of single chain antibodies (U.S. Pat. No. 4,946,778) can be adapted to produce single-chain antibodies specific for the VEGFV protein.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci.* 86:3833–3837, 1989)), and Winter G and Milstein C., (*Nature* 349:293–299, (1991)).

Antibody fragments which contain specific binding sites for VEGFV protein may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W. D. et al., *Science* 256:1275–1281, (1989)).

B. Diagnostic applications of antibodies

A variety of protocols for competitive binding or immunoradiometric assays using either polyclonal or monoclonal antibodies with established specificities are well known in the art. Such immunoassays typically involve the formation of complexes between VEGFV product and its specific antibody and the measurement of complex formation. A two-site, monoclonal-based immunoassay utilizing monoclonal antibodies reactive to two noninterfering epitopes on a specific VEGFV product is preferred, but a competitive binding assay may also be employed. These assays are described in Maddox D. E., et al., (*J. Exp. Med.* 158:1211, (1983)).

Antibodies which specifically bind VEGFV product are useful for the diagnosis of conditions or diseases characterized by over expression of VEGFV as well as for detection of diseases in which the proportion between the amount of the known VEGF and the novel VEGF variant of the invention is altered. Alternatively, such antibodies may be used in assays to monitor patients being treated with VEGFV product, its activators, or its deactivators. Diagnostic assays for VEGFV protein include methods utilizing the antibody and a label to detect VEGFV product in human body fluids or extracts of cells or tissues. The products and antibodies of the present invention may be used with or without modification. Frequently, the proteins and antibodies will be labeled by joining them, either covalently or noncovalently, with a reporter molecule. A wide variety of reporter molecules are known in the art.

A variety of protocols for measuring VEGFV product, using either polyclonal or monoclonal antibodies specific for the respective protein are known in the art. Examples include enzyme-linked immunosorbent assay (ELISA), radioimmunoassay (RIA), and fluorescent activated cell sorting (FACS). As noted above, a two-site, monoclonal-based immunoassay utilizing monoclonal antibodies reactive to two non-interfering epitopes on VEGFV product is preferred, but a competitive-binding assay may be employed. These assays are described, among other places, in Maddox, et al. (supra). Such protocols provide a basis for diagnosing altered or abnormal levels of VEGFV product expression. Normal or standard values for VEGFV product expression are established by combining body fluids or cell extracts taken from normal subjects, preferably human, with antibody to VEGFV product under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of VEGFV present in a body fluid sample, in order to determine whether it is being overexpressed or underexpressed in the tissue, or as an indication of how VEGFV levels are responding to drug treatment.

C. Therapeutic uses of antibodies

In addition to their diagnostic use the antibodies may have a therapeutical utility in blocking or decreasing the activity of the VEGFV product in pathological conditions where beneficial effect can be achieved by such a decrease.

The antibody employed is preferably a humanized monoclonal antibody, or a human MAb produced by known globulin-gene library methods. The antibody is administered typically as a sterile solution by IV injection, although other parenteral routes may be suitable. Typically, the antibody is administered in an amount between about 1–15 mg/kg body weight of the subject. Treatment is continues, e.g., with dosing every 1–7 days, until a therapeutic improvement is seen.

Although the invention has been described with reference to specific methods and embodiments, it is appreciated that various modifications and changes may be made without departing from the invention.

What is claimed is:

1. An isolated polypeptide consisting of the amino acid depicted in SEQ ID NO: 2.

2. A composition comprising a carrier and the polypeptide of claim 1.

3. A method for stimulating proliferation and differentiation of vascular endothelial cells, comprising administering to the individual a composition comprising a polypeptide comprising the amino acid sequence of SEQ ID NO: 2.

4. A method for identifying candidate compounds capable of binding to the VEGFV product and modulating its activity comprising:

(a) providing a protein or polypeptide of claim 1;

(b) contacting the candidate compounds with said amino acid sequence; and (c) determining the effect of each of said candidate compounds on the biological activity of said protein or polypeptide and selecting those compounds affect said biological activity.

5. The method according to claim 4, wherein the compound is an activator and the measured effect is increase in the biological activity.

6. The method according to claim 4, wherein the compound is a deactivator and the measured effect is decrease in the biological activity.

* * * * *

SEQUENCE LISTING

<160> NUMBER OF SEQ ID NOS: 2

<210> SEQ ID NO 1
<211> LENGTH: 649
<212> TYPE: DNA
<213> ORGANISM: Homo sapiens

<400> SEQUENCE: 1
taagcattgt cccttccaaa ggagtgccag gctcctggct atgttttctc actagcccta 60
gagccatcat cctggagttg gctccatccc attgttgctg ccaccacaag tcccccacaa 120
gaccaagtcc ctgacccagg gaggctatgg gagcccccaa cagaggtagc caagagcccc 180
aaaccaagac aaccggccat ggagagggag aagtgctaaa gtcagggcca cttacttttc 240
ttgtcttgct ctatctttct ttggtctgca ttcacatttg ttgtgctgta ggaagctcat 300
ctctcctatg tgctggcctt ggtgaggttt gatccgcata atctgcatgg tgatgttgga 360
ctcctcagtg ggcacacact ccaggccctc gtcattgcag cagcccccgc atcgcatcag 420
gggcacacag gatggcttga agatgtactc gatctcatca gggtactcct ggaagatgtc 480
caccagggtc tcgattggat ggcagtagct gcgctgatag acatccatga acttcaccac 540
ttcgtgatga ttctgccctc ctccttctgc catgggtgca gcctgggacc acttggcatg 600
gtggaggtag agcagcaagg caaggctcca atgcaccccc aaaaaaaaa 649

<210> SEQ ID NO 2
<211> LENGTH: 141
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1 5 10 15

Tyr Leu His His Ala Lys Trp Ser Gln Ala Ala Pro Met Ala Glu Gly
20 25 30

Gly Gly Gln Asn His His Glu Val Val Lys Phe Met Asp Val Tyr Gln
35 40 45

Arg Ser Tyr Cys His Pro Ile Glu Thr Leu Val Asp Ile Phe Gln Glu
50 55 60

Tyr Pro Asp Glu Ile Glu Tyr Ile Phe Lys Pro Ser Cys Val Pro Leu
65 70 75 80

Met Arg Cys Gly Gly Cys Cys Asn Asp Glu Gly Leu Glu Cys Val Pro
85 90 95

```
                                    -continued

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys
    130                 135                 140
```